(12) United States Patent
Panchal et al.

(10) Patent No.: US 10,934,259 B2
(45) Date of Patent: Mar. 2, 2021

(54) PROCESS FOR PREPARATION OF BOSCALID ANHYDRATE FORM I AND BOSCALID ANHYDRATE FORM II

(71) Applicant: UPL LIMITED, West Bengal (IN)

(72) Inventors: Digish Manubhai Panchal, Maharashtra (IN); Rakesh Bhulabhai Patel, Maharashtra (IN); Jaidev Rajnikant Shroff, Dubai (AE); Vikram Rajnikant Shroff, Dubai (AE)

(73) Assignee: UPL LIMITED, West Bengal (IN)

( * ) Notice: Subject to any disclaimer, the term of this patent is extended or adjusted under 35 U.S.C. 154(b) by 0 days.

(21) Appl. No.: 16/337,571

(22) PCT Filed: Sep. 26, 2017

(86) PCT No.: PCT/IB2017/055821
§ 371 (c)(1),
(2) Date: Mar. 28, 2019

(87) PCT Pub. No.: WO2018/060836
PCT Pub. Date: Apr. 5, 2018

(65) Prior Publication Data
US 2020/0031772 A1    Jan. 30, 2020

(30) Foreign Application Priority Data
Sep. 28, 2016   (IN) .............................. 201631033175

(51) Int. Cl.
*C07D 213/56*   (2006.01)

(52) U.S. Cl.
CPC ........ *C07D 213/56* (2013.01); *C07B 2200/13* (2013.01)

(58) Field of Classification Search
CPC .................................................... C07D 213/56
USPC .......................................................... 546/323
See application file for complete search history.

(56) References Cited

U.S. PATENT DOCUMENTS

| 7,087,239 B2 | 8/2006 | Bratz et al. |
| 7,241,896 B2* | 7/2007 | Mayer ................. C07D 213/82 546/315 |
| 7,501,384 B2 | 3/2009 | Mayer et al. |
| 2006/0154825 A1 | 7/2006 | Mayer et al. |
| 2011/0054183 A1 | 3/2011 | Reichert et al. |

FOREIGN PATENT DOCUMENTS

| CN | 103980192 A | 8/2014 |
| CN | 104478797 | 4/2015 |
| CN | 104920366 A | 9/2015 |
| GB | 2536979 A | 10/2016 |
| GB | 2539022 A | 12/2016 |
| WO | 2017193619 A1 | 11/2017 |

OTHER PUBLICATIONS

Pharmaceutical Tech. (2006), vol. 30(10), pp. 1-3.*
Caira, Topics in Cur. Chem., vol. 198 (1998) pp. 163-208.*
International Search Report and Written Opinion; International Application No. PCT/IB2017/055821, International Filing Date Sep. 26, 2017; dated Jan. 9, 2018; 15 pages.

* cited by examiner

*Primary Examiner* — Taofiq A Solola
(74) *Attorney, Agent, or Firm* — Cantor Colburn LLP

(57) ABSTRACT

The present invention relates to a novel process for preparation of boscalid anhydrate form I and boscalid anhydrate form II.

8 Claims, No Drawings

PROCESS FOR PREPARATION OF BOSCALID ANHYDRATE FORM I AND BOSCALID ANHYDRATE FORM II

CROSS REFERENCE TO RELATED APPLICATIONS

This application is a National Stage application under 35 U.S.C. § 371 of PCT/IB2017/055821, filed on Sep. 26, 2017, which claims the benefit of Indian Application No. 201631033175, filed on Sep. 28, 2016, both of which are incorporated by reference in their entirety herein.

TECHNICAL FIELD OF THE INVENTION

The present invention relates to a novel process for preparation of boscalid anhydrate form I and boscalid anhydrate form II.

BACKGROUND OF THE INVENTION

Solid state compounds exist in different physical forms such as crystalline (regular geometric lattice), and amorphous forms (irregular geometric lattice). This phenomenon is called polymorphism. It is derived from the greek word "polus" means "many" and "morph" means "shape". Thus it is defined as the ability of a substance to exist in two or more crystalline forms that have different arrangements or conformations of the molecules in the crystal lattice.

Polymorphic forms of a substance can have different chemical and physical properties, including melting point, chemical reactivity, solubility, optical, electrical and mechanical properties, vapor pressure, stability, and density.

2-Chloro-N-(4'-chlorobiphenyl-2-yl)nicotinamide is a succinate dehydrogenase inhibitor (SDHI) fungicide commonly known as boscalid. Boscalid is known to exist in three crystalline forms—boscalid anhydrate form I, boscalid anhydrate form II, boscalid monohydrate form and an amorphous form.

Boscalid anhydrate form I is used as starting material for preparing boscalid monohydrate form which is suitable for making SC formulations. Further form I is used for preparing boscalid anhydrate form II which is found to be suitable for making solid formulations.

U.S. Pat. No. 7,087,239B2 discloses boscalid monohydrate form I and its preparation from an organic solvent selected from dioxane, tetrahydrofuran, dimethylformamide, N-methylpyrrolidone, benzene, toluene and xylene.

U.S. Pat. No. 7,501,384B2 discloses boscalid anhydrate form II and its preparation from a polar protic solvent such as an alcohol, glycol, ketone, ether, ester, amide or dimethyl sulfoxide or a mixture thereof.

These processes available in the prior art require the use of large volumes of expensive solvents. Moreover, these processes do not give satisfactory yields. Hence there is a need to develop an economical process to prepare boscalid anhydrate form I and boscalid anhydrate form II.

OBJECTS OF THE INVENTION

Accordingly, it is an object of the present invention to prepare boscalid anhydrate form I in substantially pure form.

It is an object of the present invention to prepare boscalid anhydrate form II in substantially pure form.

It is an object of the present invention to develop an economical process to produce boscalid anhydrate forms I and II.

It is an object of the present invention to develop a process to obtain boscalid anhydrate forms I and II in better yield.

SUMMARY OF THE INVENTION

A process for preparing boscalid anhydrate form I comprising crystallizing boscalid from a halogenated hydrocarbon solvent.

A process for preparing boscalid anhydrate form I comprising:
 a) dissolving boscalid in a halogenated hydrocarbon solvent at or above room temperature;
 b) cooling and stirring the solution at a first predetermined speed; and
 c) effecting crystallization.

A process for preparing boscalid anhydrate form II comprising crystallizing boscalid from a halogenated hydrocarbon solvent.

A process for preparing boscalid anhydrate form II comprising:
 a) dissolving boscalid in a halogenated hydrocarbon solvent at or above room temperature;
 b) cooling and stirring the solution at a second predetermined speed; and
 c) effecting crystallization.

DETAILED DESCRIPTION OF THE INVENTION

The inventors of the present invention surprisingly found out that substantially pure boscalid anhydrate form I and boscalid anhydrate form II can be selectively prepared by crystallizing from a halogenated hydrocarbon solvent under selective stirring and cooling conditions.

Accordingly, the present invention provides a process for the preparation of boscalid anhydrate form I by crystallizing boscalid from a halogenated hydrocarbon solvent.

Further, the present invention also provides a process for the preparation of boscalid anhydrate form II by crystallizing boscalid from a halogenated hydrocarbon solvent.

Boscalid anhydrate form I refers to monoclinic boscalid anhydrate modification I with melting point 144-145° C.

Boscalid anhydrate form II refers to monoclinic boscalid and anhydrate modification II with melting point 147-148° C.

In an embodiment of the present invention, boscalid anhydrate form I is prepared by process comprising:
 a) dissolving boscalid in a halogenated hydrocarbon solvent at or above room temperature;
 b) cooling and stirring the solution at a first predetermined speed; and
 c) effecting crystallization.

In another embodiment of the present invention, boscalid anhydrate form I is prepared by process comprising:
 a) dissolving boscalid in a halogenated hydrocarbon solvent, optionally in presence of water, at or above room temperature;
 b) cooling and stirring the solution at a first predetermined speed; and
 c) effecting crystallization.

Various methods for preparing boscalid of step a) are known in literature.

In an embodiment of the present invention, boscalid of step a) comprises a mixture of boscalid anhydrate form I and boscalid anhydrate form II.

Therefore, in this embodiment, the present invention provides a process for preparing boscalid anhydrate form I comprising crystallizing a mixture of boscalid anhydrate form I and boscalid anhydrate form II from a halogenated hydrocarbon solvent.

In yet another embodiment of the present invention, boscalid of step a) comprises boscalid anhydrate form II.

Therefore, in this embodiment, the present invention provides a process for preparing boscalid anhydrate form I comprising crystallizing boscalid anhydrate form II from a halogenated hydrocarbon solvent.

According to another embodiment the solvents of step a) comprises a mixture of halogenated hydrocarbons.

In another embodiment, the solvents of step a) comprises a mixture of halogenated hydrocarbons and water.

In an embodiment of the present invention, in step a) the halogenated hydrocarbon solvent is selected from halogenated lower hydrocarbons containing $C_1$ to $C_6$ carbon atoms.

In a preferred embodiment of the present invention, the halogenated hydrocarbon solvent is selected from but not limited to dichloromethane, dichloroethane, chloroform, and chlorobenzene.

In an embodiment of the present invention, in step a), boscalid is dissolved at temperature from about 25° to about 120° C.

In an embodiment stirring of step b) is performed at a predetermined speed of 400-700 rpm, preferably at a speed of 450-650 rpm.

In an embodiment of the present invention, in step b), solution of boscalid is cooled to a temperature which varies from about 20° C. to about 50° C.

In an embodiment of the present invention, step b), cooling of boscalid solution is carried out in a time period of 15 minutes to 2 hours.

According to an embodiment of the present invention, in step c), the crystallization is effected at a temperature which varies from about −15° C. to about 30° C.

According to an embodiment of the present invention, in step c), the crystallization is effected by sudden cooling.

In another embodiment of the present invention, in step c), the crystallization of boscalid anhydrate form I is carried out in a time period of 15 minutes to 2 hours.

According to one embodiment of the present invention, in step c), the crystallization is initiated by seeding the solution with boscalid anhydrate form I.

In an embodiment of the present invention the boscalid anhydrate form I crystals are isolated by filtration.

In an embodiment, the chemical procedure which may be used to prepare boscalid anhydrate form I is not particularly limiting and may be carried out by a skilled technician as per the standard conventional procedure as long as the criticality of the selected solvent, stirring speed and cooling condition is maintained.

The present invention further provides a process for preparation of boscalid anhydrate form II.

In an embodiment of the present invention, boscalid anhydrate form II is prepared by a process comprising the following steps:
 a) dissolving boscalid in a halogenated hydrocarbon solvent at or above room temperature;
 b) cooling and stirring the solution at a predetermined speed; and
 c) effecting crystallization In an embodiment of the present invention, boscalid anhydrate form II is prepared by a process comprising the following steps:
 a) dissolving boscalid in a halogenated hydrocarbon solvent optionally in presence of water at or above room temperature;
 b) cooling and stirring the solution at a predetermined speed; and
 c) effecting crystallization In another embodiment of the present invention, boscalid of step a) comprises a mixture of boscalid anhydrate form I and boscalid anhydrate form II.

In yet another embodiment of the present invention, boscalid of step a) comprises boscalid anhydrate form I.

According to another embodiment, solvents of step a) comprises a mixture of halogenated hydrocarbons.

In another embodiment, solvents of step a) comprises a mixture of halogenated hydrocarbon solvents and water.

In an embodiment of the present invention, in step a) the halogenated hydrocarbon solvent is selected from halogenated lower hydrocarbons containing $C_1$ to $C_6$ carbon atoms.

In a preferred embodiment of the present invention, the halogenated hydrocarbon solvent is selected from but not limited to dichloromethane, dichloroethane, chloroform and chlorobenzene.

In an embodiment of the present invention, in step a), boscalid is dissolved at temperature from about 25° C. to about 120° C.

In an embodiment, stirring of step b) is performed at a predetermined speed of 40-130 rpm, preferably at a speed of 50-100 rpm.

In an embodiment of the present invention, in step b), solution of boscalid is cooled to a temperature which varies from about 20° C. to about 50° C.

In an embodiment of the present invention, in step b), cooling of boscalid solution is carried out in a time period of about 2 hours to about 4 hours.

According to another embodiment of the present invention, in step c) the crystallization is effected at a temperature which varies from about −15° C. to about 30° C.

According to an embodiment of the present invention, in step c), the crystallization is effected by gradual cooling.

In another embodiment of the present invention, in step c), the crystallization of boscalid anhydrate form II is carried out in a time period of about 1 hour to about 4 hours.

According to another embodiment of the present invention, the crystallization is effected by seeding the solution with boscalid anhydrate form II.

In an embodiment of the present invention the boscalid anhydrate crystal form II are isolated by filtration.

In an embodiment, the chemical procedure which may be used to prepare boscalid anhydrate form II is not particularly limiting and may be carried out by a skilled technician as per the standard conventional procedure as long as the criticality of the selected solvent, stirring speed and cooling condition is maintained.

Thus, the present invention provides a process for the preparation of boscalid anhydrate form I and/or boscalid anhydrate form II selectively by crystallizing boscalid from at least one halogenated hydrocarbon solvent, optionally in admixture with water. In an embodiment, the selectivity between boscalid anhydrate form I and boscalid anhydrate form II is achieved by selecting the above-described stirring and cooling conditions, which are different for boscalid anhydrate form I and boscalid anhydrate form II, to selectively lead to either substantially pure boscalid anhydrate form I or substantially pure boscalid anhydrate form II.

The invention shall now be described with reference to the following specific examples. It should be noted that the examples appended below illustrate rather than limit the invention and that those skilled in the art will be able to design many alternative embodiments without departing from the scope of the present invention.

EXAMPLES

The following examples described below are to illustrate the embodiments of the present invention and are not limiting the scope of the present invention. The product has been characterized using DSC (Differential Scanning Calorimetry) and FT-IR.

Example 1: Preparation of Boscalid

To a stirred solution of 4-chlorobiphenyl-2-yl-amine (164.0 g, 0.805 mol) in dichloroethane (812.0 g) was added triethylamine (96.0 g, 0.950 mol) at room temperature. The reaction mixture was cooled to 10° C. and 2-chloronicotinyl chloride (179.0 g, 1.017 mol) in dichloroethane (268.0 g) was drop wise added to it for 5-6 h. The reaction mixture was refluxed for 1 h. The reaction was cooled to 30° C. and water (278.0 g) was added to it. The mixture was heated to 60-70° C. for 30 min and then stirred for 15 minutes. The mixture was cooled to room temperature and aqueous layer was separated. The organic layer was washed with 5% aqueous sodium hydroxide solution followed by water. The organic layer was dried on sodium sulphate.

Example 2: Preparation of Boscalid Anhydrate Form

In a reaction assembly, the organic layer (obtained from Example 1) was diluted with dichloroethane (1326.0 g) and stirred above room temperature. The solution was stirred at 450-600 rpm and cooled to 25-35° C. in 1 hour. After crystal formation was observed, the solution, was suddenly cooled to −10° to 5° C. The crystals were stirred at same temperature for 1 hour. The crystalline solid was filtered and dried to obtain 230.0 g of boscalid anhydrate form I.
Melting point 145.07° C.
IR (cm$^{-1}$): 923, 1313, 1652

Example 3: Preparation of Boscalid Anhydrate Form II

In a reaction assembly, the organic layer (obtained from Example 1) was diluted with dichloroethane (1326.0 g) and stirred above room temperature. The solution is was stirred at 50-100 rpm and gradually cooled to 35-45° C. in 3 hours. After crystals formation were observed, it was maintained at same temperature for 1 h. The crystals were gradually cooled to −10° to 5° C. and stirred at same temperature for 1 hour. The crystalline solid was filtered and dried to obtain 237.0 g of boscalid anhydrate form II.
Melting point: 147.57° C.
IR (cm$^{-1}$): 867, 917, 1677

Example 4: Preparation of Boscalid Anhydrate Form I from a Mixture of Boscalid Anhydrate Form I and Boscalid Anhydrate Form II A mixture of boscalid anhydrate form I and boscalid anhydrate form II (250.0 g, 0.728 mol) was charged in a reaction assembly. To this mixture was added dichloromethane (2250.0 g) and stirred at room temperature till dissolution. The solution was stirred at 450-600 rpm and cooled to 25-35° C. in 1 hour. After crystal formation was observed, the solution was suddenly cooled to −10° to 5° C. The crystals were stirred at same temperature for 1 hour. The crystalline solid was filtered and dried to obtain 200.0 g of boscalid anhydrate form I.
Melting point: 145.09° C.
IR (cm$^{-1}$): 924, 1313, 1651

Example 5: Preparation of Boscalid Anhydrate Form II from Mixture of Boscalid Anhydrate Form I and Form II A mixture of boscalid anhydrate form I and boscalid anhydrate form 11 (250.0 g, 0.728 mol) was charged in a reaction assembly. To this mixture was added dichloroethane (1000.0 g) and stirred above room temperature till dissolution. The solution was stirred at 50-100 rpm and gradually cooled to 35-45° C. in 3 hours and maintained at same temperature for 1 h. After crystals formation were observed, it was maintained at same temperature for 1 h. The crystals were gradually cooled to −10° to 5° C. and stirred for 1 hour. The crystalline solid was filtered and dried to obtain 225.0 g of boscalid anhydrate form II.
Melting point: 147.50° C.
IR (cm$^{-1}$): 867, 916, 1675

Example 6: Preparation of Boscalid Anhydrate Form I from Boscalid Anhydrate Form II A mixture of boscalid anhydrate form II (250.0 g, 0.728 mol) in chlorobenzene (2000.0 g) was stirred above room temperature till dissolution. The solution was stirred at 450-600 rpm and cooled to 25-35° C. in 1 hour. After crystal formation was observed, the solution was suddenly cooled to −10° to 5° C. The crystals were stirred at same temperature for 30 minutes to 1 hour. The crystalline solid was filtered and dried to obtain 227.0 g of boscalid anhydrate form I.
Melting point: 145.06° C.
IR (cm$^{-1}$): 922, 1314, 1651

Example 7: Preparation of Boscalid Anhydrate Form II from Boscalid Anhydrate Form I A mixture of boscalid anhydrate form I (250.0 g, 0.728 mol) in chloroform (1000.0 g) and water (7.0 g) was stirred above room temperature till dissolution. The solution was stirred at 50-100 rpm and gradually cooled to 35-45° C. in 3 hours. After crystals formation were observed, it was maintained at same temperature for 1 h. The crystals were gradually cooled to −10° to 5° C. in 1 to 2 hours and stirred at same temperature for 30 minutes to 1 hour. The crystalline solid was filtered and dried to obtain 228.0 g of boscalid anhydrate form II.
Melting point: 147.48° C.
IR (cm$^{-1}$): 869, 916, 1676

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The invention claimed is:
1. A process for the preparation of boscalid anhydrate form I, the process comprising

(a) dissolving a boscalid starting material in dichloromethane, dichloroethane, chloroform, or chlorobenzene, at or above room temperature to provide a boscalid solution;

(b) cooling the boscalid solution and stirring the solution at a speed of 400-700 rpm in a time period of 15 minutes to 2 hours until crystal formation is observed; and (c) effecting crystallization by rapid cooling to provide a solid crystalline product from the stirred solution, wherein the solution is rapidly cooled to a temperature between −10° C. to 5° C. to effect the crystallization;

wherein said boscalid starting material is a mixture of boscalid anhydrate from I and boscalid anhydrate form II, or said boscalid starting material is boscalid anhydrate form II, and wherein the solid crystalline product is boscalid anhydrate form II having a melting point of 144-145° C.

2. The process of claim 1, comprising dissolving the boscalid at a temperature between about 25° and about 120° C. in step a).

3. The process of claim 1, wherein in step (b), cooling is to a temperature between about 20° C. and about 50° C.

4. The process of claim 1, wherein said crystallization in step (c) is initiated by seeding the solution with boscalid anhydrate form I.

5. A process for the preparation of boscalid anhydrate form II, the process comprising (a) dissolving a boscalid starting material in dichloromethane, dichloroethane, chloroform, or chlorobenzene, at or above room temperature, (b) cooling the boscalid solution and stirring the solution at a speed of 40-130 rpm in a time period of 2 hours to 4 hours until crystal formation is observed; and (c) effecting crystallization by gradual cooling to provide a solid crystalline product from the stirred solution, wherein the solution is gradually cooled to a temperature between −10° C. to 5° C. to effect the crystallization;

wherein said boscalid starting material is a mixture of boscalid anhydrate from I and boscalid anhydrate form II, or said boscalid starting material is boscalid anhydrate form I, and wherein the solid crystalline product is boscalid anhydrate form II having a melting point of 147-148° C.

6. The process of claim 5, comprising dissolving at a temperature between about 25° and about 120° C. in step a).

7. The process of claim 5, wherein in step (b), cooling is to a temperature between about 20° C. to about 50° C.

8. The process of claim 5, wherein said crystallization in step (c) is initiated by seeding the boscalid solution with boscalid anhydrate form II.

* * * * *